United States Patent [19]

Sasaki et al.

[11] 4,207,446

[45] Jun. 10, 1980

[54] GROUNDED TANK TYPE GAS CIRCUIT BREAKER

[75] Inventors: Kouji Sasaki; Seizo Nakano; Michio Moriya, all of Hitachi, Japan

[73] Assignee: Hitachi, Limited, Japan

[21] Appl. No.: 817,744

[22] Filed: Jul. 21, 1977

[30] Foreign Application Priority Data

Jul. 26, 1976 [JP] Japan ................................ 51-88219

[51] Int. Cl.² ..................... H01H 33/54; A01H 33/16

[52] U.S. Cl. ......................... 200/148 B; 200/144 AP; 200/148 R

[58] Field of Search ........... 200/148 R, 148 A, 148 B, 200/145, 144 AP

[56] References Cited

U.S. PATENT DOCUMENTS

| | | | |
|---|---|---|---|
| 3,903,387 | 9/1975 | Sasaki et al. | 200/145 |
| 4,007,346 | 2/1977 | Gaigg | 200/145 |
| 4,103,128 | 7/1978 | Kosaku | 200/144 AP |

*Primary Examiner*—Robert S. Macon
*Attorney, Agent, or Firm*—Craig and Antonelli

[57] ABSTRACT

A grounded tank type gas circuit breaker comprises a grounded tank filled with a dielectric gas and having an opening airtightly sealed by a detachable cap, a capacitor unit electrically and mechanically connected at one end to the inner wall surface of the cap, and interrupting means mounted in the tank and electrically connected to the other end of the capacitor unit.

5 Claims, 11 Drawing Figures

GROUNDED TANK TYPE GAS CIRCUIT BREAKER

LIST OF PRIOR REFERENCES (37 CFR 1.56 (a))

The following reference is cited to show the state of the art: U.S. Pat. No. 3,903,388 McConnell Sept. 2, 1975 200/148B; 200/145

This invention relates to a grounded tank type gas circuit breaker comprising a grounded tank and interrupting means electrically insulated from, and mounted in, the tank. More particularly, the invention pertains to a circuit breaker of this kind with a novel construction for improving the breaker performance at the time of a short line fault or for mounting capacitor means consisting a potential device.

With the growing demand for electric energy in recent years, power transmission lines of higher capacities for higher voltages have come into use.

Keeping pace with this trend, higher-voltage higher-capacity circuit breakers have been introduced for the protection of equipment associated with this lines.

Where the power transmission capacity of a line is increased, the circuit breaker is required to satisfy very severe conditions for interrupting the circuit in case of a short line fault. When the current that results from that abnormal condition is interrupted, a recovery voltage with a very high initial rate of rise is applied between the poles of the interrupting means.

It is well known that one way of improving the circuit-breaker performance for the short line fault is to control the initial rate of rise of the recovery voltage. To be more concrete, the method consists of connecting a capacitor between the conductors of the circuit breaker and the ground.

In the conventional method as shown in U.S. Pat. No. 3,903,388, the capacitor is merely mounted within an open space in a spherical tank. Thus, difficulties have been involved in disposing the capacitor of a circuit breaker within a tank ideally designed to eliminate such an open space within the vessel. If the capacitor is to be received, the grounded tank must be designed anew. Moreover, the breaker must be disassembled whenever such a capacitor is to be mounted or demounted.

Usually in the neighborhood of each of the circuit breakers constituting a transmission substation, a potential device is installed for measuring the voltage. A wellknown potential device for this purpose is of the coupling capacitor type. As the name implies, the device comprises a primary capacitor and a secondary capacitor, which are both connected in series between the line and the ground so that the voltage divided by the capacitors may be read out.

The potential device of this kind is conventionally built independently of the circuit breaker.

Thus, a transmission substation includes capacitors for a variety of purposes installed in the vicinity of the circuit breakers. Except for the above-mentioned capacitor for restricting the initial rate of rise of the recovery voltage, those capacitors are independently built, necessitating separate containers and spaces for installation and hence a large overall area for the substation.

It is an object of this invention to provide a grounded tank type gas circuit breaker in which a capacitor can be simply mounted without the need of increasing the diameter of the grounded tank.

Another object of the invention is to provide a grounded tank type gas circuit breaker in which a capacitor for controlling the initial rate of rise of the recovery voltage can be mounted and demounted in a simple way.

Still another object of the invention is to provide a grounded tank type gas circuit breaker in which the primary capacitor of a coupling capacitor potential device can be simply mounted and demounted.

Yet another object of the invention is to provide a grounded tank type gas circuit breaker including a capacitor utilizable for the assembling work.

According to the invention, the grounded tank type gas circuit breaker includes a grounded tank having an opening and a capacitor unit introduced into the tank through the opening and electrically connected at one end to the conductor of an interrupting unit. The capacitor unit can be taken out of the tank by removing a detachable cap airtightly fastened to the flange of the opening. In a most preferred embodiment the flanged opening is airtightly closed by a cap, and the other end of the capacitor unit is electrically and mechanically connected to this cap. This construction permits the capacitor unit to be mounted and demounted simultaneously with the attachment and detachment of the cap. The cap may be shaped like a container bulging from the grounded tank to provide a sufficient space to contain the capacitor unit, regardless of the tank size.

The arrangement or construction described above proves effective with grounded tank type gas circuit breakers, especially those using cylindrical grounded tanks with a minimum of free space within the tank shell. It applies as well to circuit breaker tanks of various other configurations. Also, the invention is applicable to circuit breakers of not only the split-phase type but also the combined three-phase type.

Figure 1:
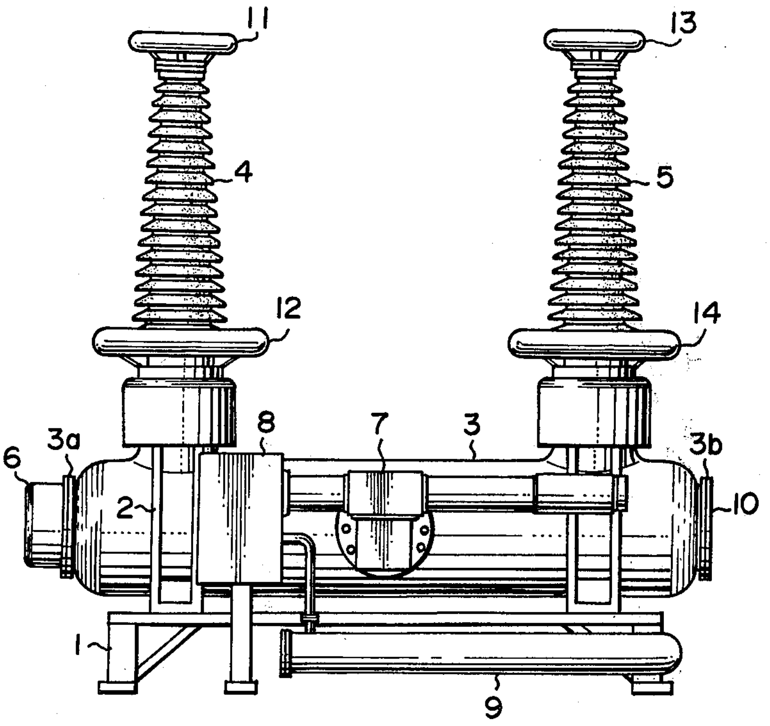
FIG. 1 is a front elevational view of an embodiment of the grounded tank type gas circuit breaker of the invention.

Referring now to FIG. 1, a grounded tank type gas blast circuit breaker is shown supported on a platform 1 fast on a foundation. Reinforcing ribs 2 are fixed to the platform 1, although other fixing and mounting means may be used other than the arrangement in this embodiment. A cylindrical grounded tank 3 has two terminal bushings 4, 5 held upright on its top. By conductors extending through the bushings 4, 5, the both end terminals of interrupting means are connected to a line not shown. Here it is assumed that the bushing 4 is on the line side and the bushing 5 on the power source side. The grounded tank 3, grounded through the plaftform 1, is at ground potential. It is filled with an arc-extinguishing dielectric gas, for example, $SF_6$ gas. At one axial end of the grounded tank 3 is formed an opening with a flange 3*a*, to which normally a mating flange of a bulged end cap 6 is detachably secured by bolts to provide an airtight seal. A box 7 containing a link motion is attached to a side wall of the middle portion of the tank 3. The link motion in the box 7 is connected to operating means in an operating box 8. The operating means may be of any desired structure. In the embodiment shown a fluid is used as a unidirectional driving power source. For the fluid supply for this purpose a fluid-filled tank 9 is installed alongside the tank 3.

Another opening at the opposite end of the grounded tank 3 has a flange 3*b* and is closed airtightly by an end cover 10. On the upper and lower ends of the two bushings 4, 5 are secured field effect-suppressing shield rings 11, 12 and 13, 14, respectively.

Figure 2:
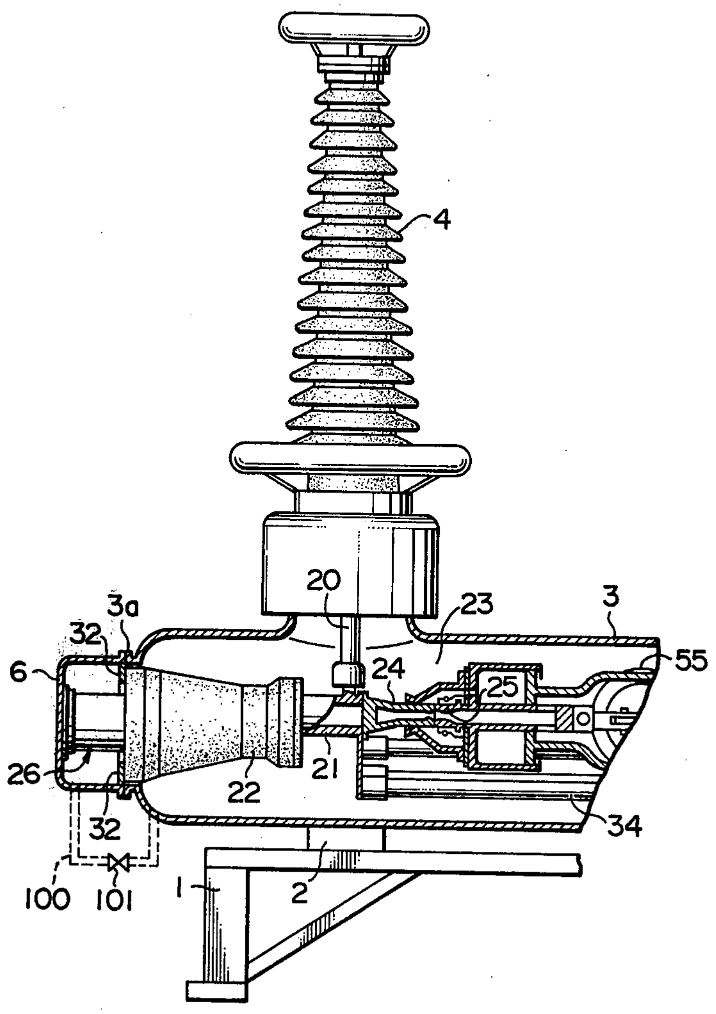
FIG. 2 is a fragmentary view, partly in vertical section, of the embodiment shown in FIG. 1.

As can be seen from FIG. 2, which is a fragmentary view, partly in section, of the circuit breaker shown in FIG. 1, the conductor 20 extending through the axial center of the bushing 4 is electrically connected to a connecting conductor 21, and these two conductors form connector means on the power transmission line side. The bushing 5 not shown here, which is disposed symmetrically with this bushing 4, is of substantially the same construction, with its center conductor and a connecting conductor electrically connected thereto likewise forming connector means on the power source side. As shown, the connector means is electrically connected to one of the contacts of an interrupting unit 23. The connecting conductor 21 is secured to one end of a cylinder 22 which serves as insulation support means. This insulation support cylinder 22 has a hollow 22*a* extending axially therethrough as in FIG. 3. The insulation support cylinder 22 not merely supports the contact of the interrupting unit but also provides protection for a capacitor unit. The insulation support means for the interrupting means may alternatively be in the form of either an insulation member partitioning the interior space of the grounded support tank 3 and the bushing 4 or a central insulation support member 55. The other end of the insulation support cylinder 22 is made fast to a disk 32, which in turn is secured to the opening flange 3*a* of the tank 3. To the other end of the connecting conductor 21 is fixed a stationary contact 24 of the interrupting unit 23. Opposite to the stationary contact 24, the interrupting unit also includes a movable contact 25, which is connected to the controls in the operating box 9 through the link motion in the box 7 as shown in FIG. 1. Since the construction of the interrupting unit is not related directly to the technical subject matter of this invention, its description in detail is omitted here. Suffice it to say that, aside from minor variation in structure, at least a pair of mutually engageable and disengageable contacts constitute the interrupting unit. In the insulation support cylinder 22 is fitted a portion of a capacitor unit 26, which portion will now be described with references to FIG. 3.

To the left end of the connecting conductor 21 is secured a current collector bracket 27 having a center opening 27*a*. The collector bracket 27, in turn, supports a generally frustoconical current collector 28 with the aid of springs 102. The current collector 28 consists of a plurality of conductors in the form of strips arranged side by side to surround the opening 27*a* of the collector bracket 27. An electrode 29 attached to the right end of the capacitor unit 26 is in contact with this current collector 28, so that one end of the capacitor unit 26 is electrically connected to the connector means. At the left end of the capacitor unit 26, its electrode 30 is mechanically and electrically connected to the bulged end cap 6. A plurality of internally threaded blind socket pieces 104 are set at given intervals in the left end portion of the insulation support cylinder 22. The disk 32, attached to the flange 3*a* of the grounded tank 3 by bolts 105, supports the insulation support cylinder 22 by bolts 106 in thread engagement with the socket pieces 104. The bulged end cap 6 is larger in inside diameter than the disk 32 and has a flange connected to the flange 3*a* by bolts 103. Although not shown, a seal member is interposed between the end cap 6 and the flange 3*a*, and is fastened together by bolts 103 to provide an airtight seal.

The left end of the capacitor unit is mechanically and electrically connected to the grounded tank 3 through the cap 6. This means that the capacitor unit 26 is electrically connected in series between the connector means and the ground, thus restricting the initial rate of rise of the recovery voltage that is applied between the poles of the interrupting unit 23 in case of a short line fault.

The bulged end cap 6 has a depth that varies with the length of the capacitor unit 26, it may take the form of a flat plate lid where a shortest capacitor unit is used. The capacitor unit 26 is an oil-filled condenser or a ceramic condenser, in either case consisting of an insulation cylinder 33 and a condenser element housed therein. With such a construction the capacitor unit 26 has a capacitance selected according to certain factors, including the number of interrupting units used and the circuit conditions. The capacitance may range, for example, between about 2000 and 2500 PF, or about ten times greater than that of a voltage-dividing capacitor 34 electrically connected in parallel with the contacts 24, 25 as shown in FIG. 2. In this connection it is to be noted that, whereas the voltage-dividing capacitor 34 is used in the embodiment shown in FIG. 2 which comprises a plurality of series-connected interrupting units, no such capacitor is provided where a single interrupting unit constitutes the interrupting means.

Figure 3:
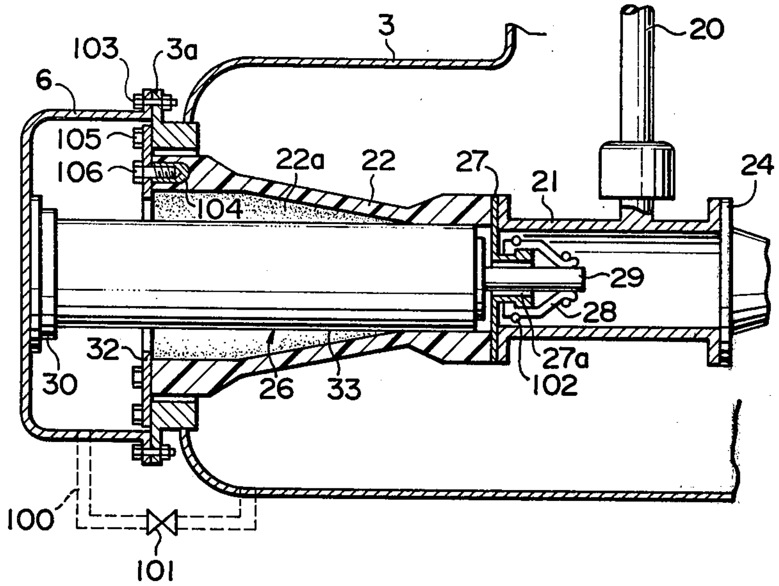
FIG. 3 is an enlarged sectional view of the essential parts of FIG. 2.

As will be obvious from FIG. 2, the interrupting unit 23 is electrically insulated from, and coaxially disposed in, the grounded tank 3, and therefore the free space left between the unit and the surrounding wall of the tank is reduced to the minimum. The capacitor unit 26 too is coaxial with the grounded tank 3, making it unnecessary to use a large-diameter tank. Where a longer or shorter capacitor unit is to be used, it is only necessary to employ a bulged end cap 6 of an increased or decreased depth, as the case may be. Moreover, because the bulged end cap 6 is detachably bolted to the flange 3*a* of the grounded tank 3 and one end of the capacitor unit 26 is mechanically secured to the cap 6, the capacitor unit 26 is mounted and demounted with extreme ease. On the other hand, as shown in FIG. 3, one end of the capacitor unit 26 is fitted in the insulation support cylinder 22, with some clearance or space provided between the remaining portion of the unit and the flaring wall portion of the cylinder. With this space the insulation support cylinder 22 serves as a guide for insertion of the capacitor unit 26 during assembling and also as a reinforcement against vibrations upward and downward as viewed in the figure. Usually, on closing the circuit between its contacts, the interrupting unit tends to transmit the impact to the side of the stationary contact, but the insulation support cylinder 22 absorbs the impact, enabling the capacitor unit 26 to have an accordingly reduced axial mechanical strength. To ensure complete protection of the capacitor unit 26 from the impact, it is desirable that the impact be absorbed at the right end of the capacitor unit 26. While the frustoconical current collector 28 which permits axial sliding motion of the electrode 29 is most desirable, the same purpose may be served alternatively by a club-shaped contact associated with an axially compressible shock-absorbing spring.

As a modification of the embodiment illustrated in FIG. 3, the electrode 29 or a part of the capacitor unit 26 at the same potential may be supported by the current collector bracket 27. As a further alternative, it is possible to attach the frustoconical current collector 28 to the right end of the capacitor unit 26 and fix a corresponding electrode to the collector bracket 27.

Figure 4:
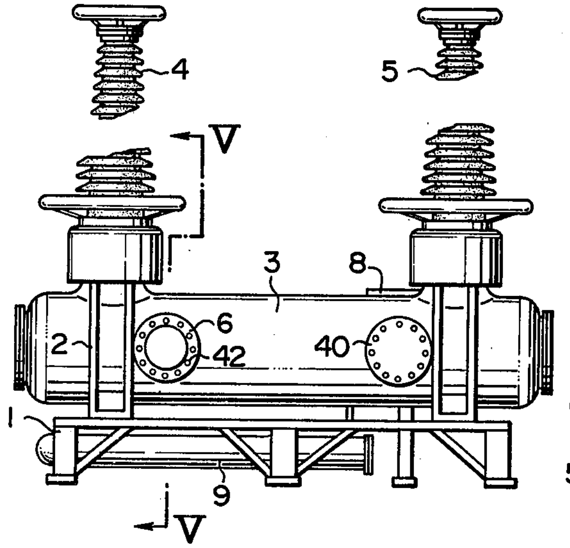
FIG. 4 is a rear view of another embodiment of the grounded tank type gas circuit breaker of the invention.

FIG. 4 depicts another embodiment of the grounded tank type gas circuit breaker of the invention, the elevation corresponding to a rear view of the circuit breaker of FIG. 1.

On the rear side of the grounded tank 3 are formed two flanged openings which are normally closed and airtightly sealed, respectively, by a bulged cap 6 and a blind cover 40 both of which are detachable. The rest of the construction is similar to that shown in FIG. 1 and therefore like parts are designated by like numerals and the description is not repeated here. The major distinctions between the two embodiments will now be explained in connection with FIG. 5.

Figure 5:
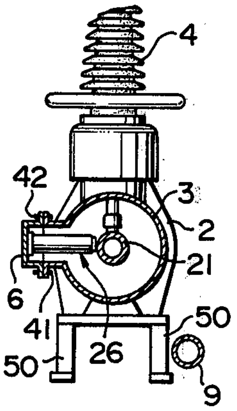
FIG. 5 is a sectional view taken on the line V—V of FIG. 4.

One of the flanged openings, 41, on the rear side of the grounded tank 3 is formed relative to a connecting conductor 21, and it is airtightly closed by a detachable cover 6 by bolts 42. To the inner wall surface of the cover 6 is electrically and mechanically connected one end of a capacitor unit 26, the other end of which being in contact with a frustoconical current collector not shown, in the same manner as with the embodiment in FIG. 3, and in electrical connection with a connecting conductor 21 forming a connector means. The relative positions of the flanged opening 41 and the connecting conductor 21 are somewhat offset as compared with the positions in FIG. 2. This is because, despite a reduction in the axial length of the interrupting means due to the improved design, the air insulation distance between the bushings 4 and 5 in FIG. 5 is kept unchanged and therefore the axial dimension of the connecting conductor 21 is increased in this second embodiment.

In the construction illustrated, the capacitor unit 26 is of necessity disposed radially of the grounded tank 3. This arrangement helps reduce the impact given from the interrupting unit axially of the capacitor unit 26. Although the capacitor unit 26 is subjected to some impact at one end, the impact is fully absorbed by the current collector assembly and the like. This advantageous effect is not achieved with the preceding embodiment but with the arrangement in which the capacitor unit 26 is disposed radially of the grounded tank 3, and the capacitor unit 26 need not be mounted horizontally. The inside diameter of the flanged opening 41 may be large enough to provide an access for the inspection of the interrupting unit.

Figure 6:
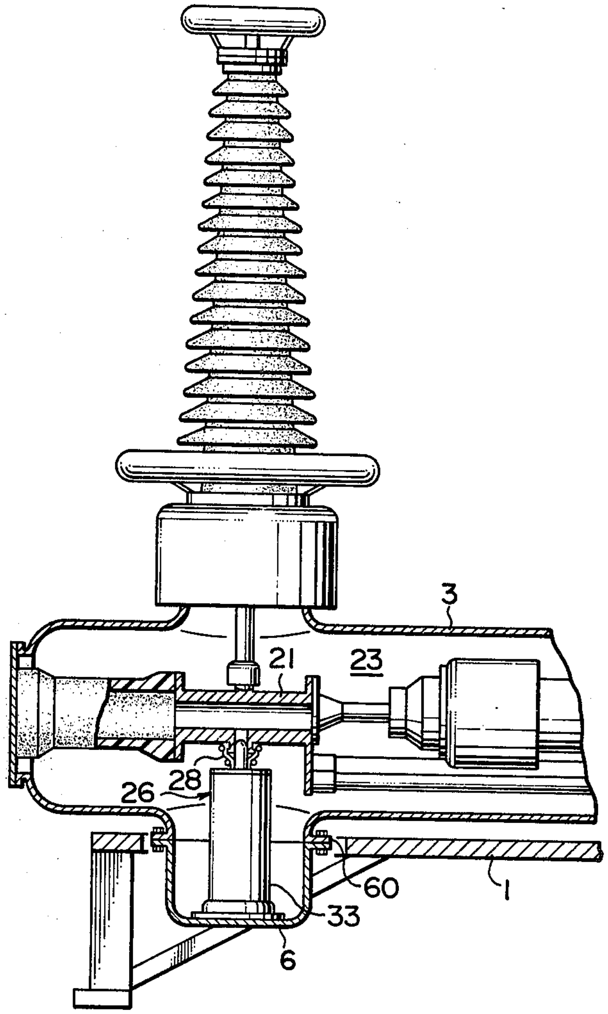
FIGS. 6 through 11 are fragmentary views, partly in vertical section, of other embodiments of the invention.

FIG. 6 shows still another embodiment of the invention. Like the embodiment in FIGS. 4 and 5, this embodiment takes the advantage of mounting the capacitor unit 26 radially of the grounded tank.

The grounded tank 3 as embodied here includes a flanged opening 60 formed in its bottom. The opening 60 is closed by a detachable cap 6. Since the cap 6 bulges downward into the platform 1, the tank 3 looks as though it does not contain the capacitor unit 26. The cap 6 extends between the legs 50 of the platform 1 shown in FIG. 5.

Figure 7:
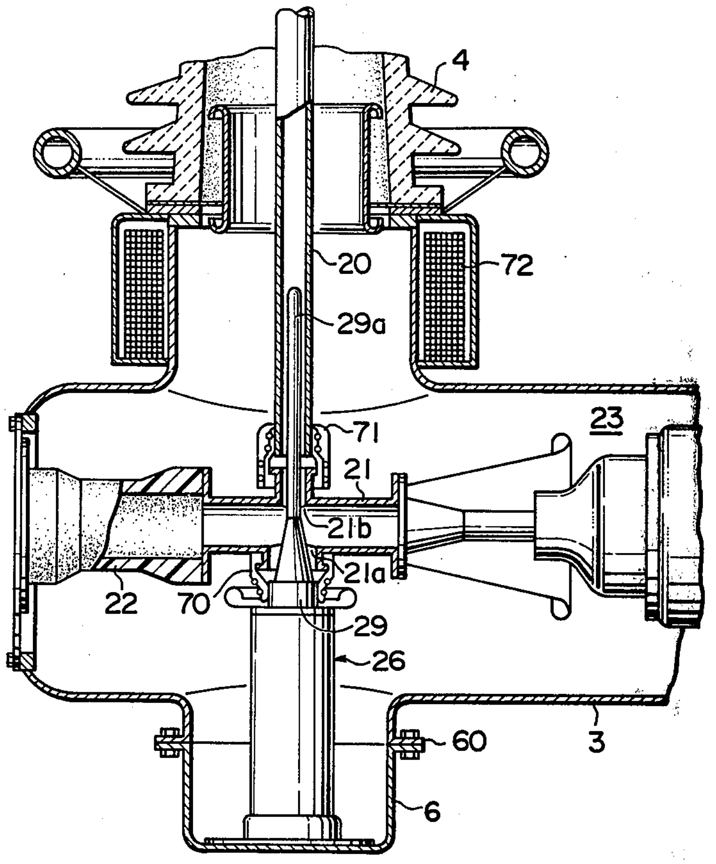

This construction relieves the impact that is transmitted from the interrupting unit 23 to the capacitor unit 26. Also, in contrast to the embodiment shown in FIG. 4, a flanged opening for the inspection of the interrupting unit can be formed aside from the opening 60 for mounting the capacitor unit, and therefore the opening for inspection may be formed at a point most accessible for the inspection. While this embodiment may be modified so that the flanged opening 60 is formed off the bottom and radially of the grounded tank 3 as in FIG. 4, the vertical location of the capacitor unit 26 offers the following advantages.

Where the capacitor unit 26 consists of an oil-filled condenser which can be made relatively small in size, the insulation cylinder 33 forming the outer casing of the capacitor unit is filled with insulation oil. With an allowance for its thermal expansion, the insulation oil is filled in the insulation cylinder 33 to such an extent that an unfilled space is left in the cylinder at ordinary temperature. Thus, if the capacitor unit 26 is mounted horizontally, the condenser element will be partly exposed to the unoccupied space within the vessel. Consequently the exposed axial portions of the element and insulation cylinder 33 will exhibit decreases in dielectric strength. Where the capacitor unit 26 is disposed vertically as shown in FIG. 6, there will be no such continuous space formed axially. The capacitor unit thus obtained is stable in performance. This principle may be appllied as embodied in FIG. 7.

In the embodiment shown, the capacitor unit 26 of the embodiment in FIG. 6 is aligned in centerline to the hollow center conductor 20 of the bushing 4.

To the flanged opening 60 of the grounded tank 3 is detachably fixed a cap 6, and one end of the capacitor unit 26 is electrically and mechanically connected to the inner wall surface of the cap 6. An electrode 29 is attached to the other end of the capacitor unit 26. The upper end portion of this electrode 29 is reduced to a diameter smaller than the inside diameter of the hollow center conductor 20 and is extended as a guide rod 29*a* into the hollow. The guide rod 29*a* rises across a connecting conductor 21, through its openings 21*a* and 21*b*. Cylindrical flanges formed on the openings of the connecting conductor 21 support frustoconical current collectors 70 and 71, respectively. Electrically the current collector 70 is in contact with the outer surface of the electrode 29, and the collector 71 is in contact with the outer surface of the center conductor 20. The coil of a current transformer is indicated at 72.

The circuit breaker as embodied here is assembled by first mounting the interrupting unit 23, connecting conductor 21, and insulation support cylinder 22 within the metallic tank 3, and then inserting the capacitor unit 26 through the flanged opening 60. In this way the electrode 29 is electrically connected to the frustoconical current collector 70. The flange of the cap 6 is airtightly fastened to the flange of the opening 60 by bolts. Next, the bushing 4 is made fast to the grounded tank 3. As shown the bushing 4 is of a hollow, gas-filled type, and its hollow is communicated with the space within the tank 3. As is well known in the art, the bushing of this type has a center conductor 20 which is secured at the upper end with the porcelain tube, the lower end of the center conductor 20 being free, out of control in position.

Therefore, the center conductor 20 of the bushing 4 and the porcelain tube are not always aligned in centerlines. This usually necessitates parallel progress of the work for connecting the porcelain tube and the grounded tank and the work for connecting the center conductor 20 and the frustoconical current collector 71. In this embodiment, however, the electrode 29 of the capacitor unit 26 has the guide rod 29a which is inserted into the hollow center conductor 20 to guide and center the same. Thereafter, the porcelain tube is fixed to the metallic tank 3, and thereby the center conductor 20 is kept in perfect contact with the frustoconical current collector 71 and the assembling work is concluded.

As stated, the alignment of the electrode of the capacitor unit 26 with the center conductor 20 in centerlines makes this embodiment simple to assemble. Although this embodiment uses gas-filled bushings, and the space within the bushing 4 and around the interrupting unit 23 is not partitioned to provide separate gas compartments, this is not a limitation to the invention as embodied in FIGS. 1 to 6. The common space may be partitioned by an insulation spacer, for example, to form separate gas compartments.

Also, while it has been stated with all of the embodiments that the bushing 4 is on the power transmission line side, the capacitor unit 26 is not necessarily connected only to the connector means of the interrupting unit on the line side. The line on the power source side is usually short, and if the line is long the same countermeasure as with the power transmission line will become necessary. In that case, the capacitor unit is connected to the connector means on both sides of the interrupting unit. In the countermeasure for only the power transmission line, too, it is desirable to design the capacitor unit so that it may be attached to the both connector means lest the interrupting unit be restricted in its disposition.

Although the embodiments of the present invention so far described are circuit breakers using bushings 4, 5 of the air insulation type, the invention is equally applicable to the circuit breakers which use metallic containers in place of the bushings, with each center conductor being insulated from the associated metallic container.

Figure 8:
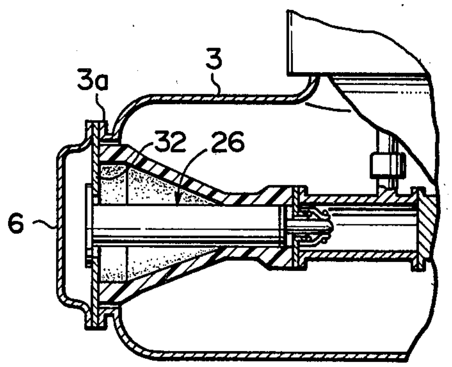
Figure 9:
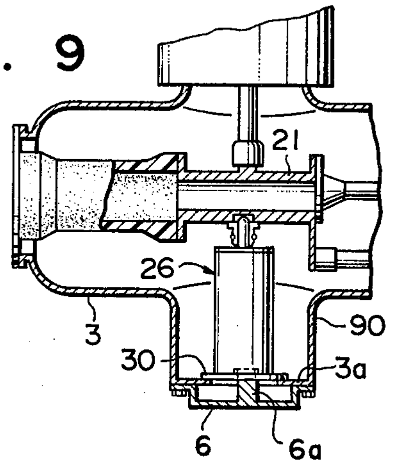

In other embodiments illustrated in FIGS. 8 and 9, one end of the capacitor unit 26 is mechanically supported by the grounded tank 3 instead of being mechanically fixed direct to the cap 6 as in all of the preceding embodiments.

The embodiment depicted in FIG. 8 is similar to the one in FIG. 3. One end of the capacitor unit 26 is detachably bolted or otherwise secured to a support disk 32 which, in turn, is fixed to the flange 3a of the grounded tank 3. The opening of the flange 3a is airtightly closed by a detachable cap 6. Although the capacitor unit 26 cannot be removed without detaching the cap 6 in advance, the removal is easily accomplished from the outside and, in this respect, the same effect as with the embodiment in FIG. 3 is achieved.

The embodiment shown in FIG. 9 resembles the one in FIG. 6. Here the capacitor unit 26 is mounted in a cylindrical extension 90 welded or otherwise connected to the grounded tank 3. An inner projection 6a of a cap detachably bolted to an inner flange 3a of the tank 3 fits in a recess formed at the bottom of the capacitor unit 26. The inner flange 3a and the lower electrode 30 of the capacitor unit 26 are not disk-shaped but elliptical or the like with large and small diameter portions, so that after the introduction into the tank extension the capacitor unit 26 may be turned through an angle of 90 deg. to the resting position shown.

Lateral displacement from the normal position of the capacitor unit 26 is controlled by the engagement of the unit with the inner projection 6a. As for the vertical displacement, the connecting conductor 21 is desirably used to provide the upper limit.

This embodiment indicates that it is not essential to fix one end of the capacitor unit 26 mechanically. The capacitor unit has only to be of a construction such that the one end is, after all, mechanically supported by the grounded tank.

The embodiments illustrated in FIGS. 8 and 9 make it possible to guide the capacitor unit 26 under visual observation from the outside during the assembling work when the capacitor unit 26 is inserted into the grounded tank 3 through an opening and the electrode at its front end is electrically connected to the connecting conductor 21. In the preceding embodiments the capacitor unit 26 is connected to the cap of a contour restricted by the necessity of airtight sealing, and therefore the leading end of the capacitor unit 26 being introduced into the tank for assembling is not in the least visible from the outside and the connection work is cumbersome. For this reason, some aid for connection, such as the insulation support cylinder 22 as shown in FIG. 3 which produces a guiding effect, or the guide rod 29a in FIG. 7 which is utilized as a guide for the capacitor unit 26, will be necessary.

Figure 10:
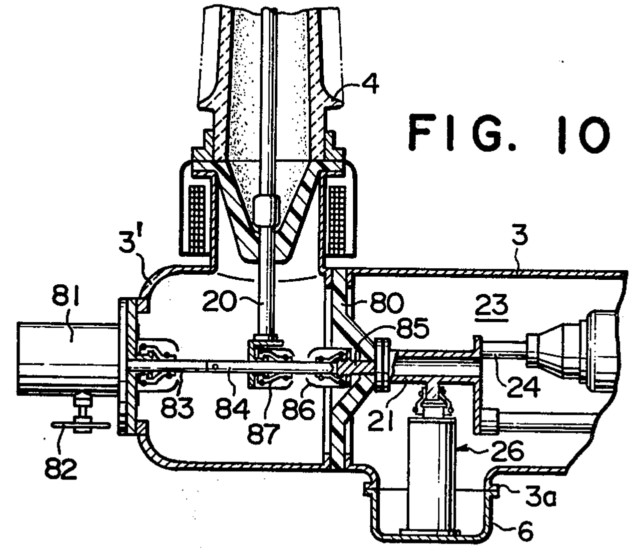

FIG. 10 shows an embodiment in which a disconnecting switch is formed axially of a grounded tank 3 containing an interrupting unit.

To an opening at the left end of the grounded tank 3 is airtightly secured one end of a second grounded tank 3', with an insulation spacer 80 disposed in between. A container 81 housing a link motion is airtightly fixed to the other end of the second grounded tank 3'. One end of the link motion in the container 81 is connected to a handwheel 82, and the other end is connected to a movable member 84 through an insulation rod 83. The handwheel 82 is turned by drives not shown. The rotation of the handwheel is converted to an axial reciprocating motion of the movable member 84.

The stationary contact 24 of the interrupting unit 23 is secured, through the connecting conductor 21, to one end of a conductor 85 set in the center of the insulation spacer 80. The other end of the conductor 85 supports a stationary member 86.

To the center conductor 20 of the bushing 4 is attached a second stationary member 87, which is slidable relative to the movable member 84 in electrical connection therewith.

The movable member 84 and the slidable member 86 constitute a disconnecting switch, which is separated gaswise from the interrupting unit by the insulation spacer 80. An opening is formed in a side wall of the grounded tank 3, and a detachable cap 6 is airtightly secured to the flange 3a of the opening. One end of the capacitor unit 26 is electrically and mechanically connected to the inner wall surface of the cap 6. The other end of the capacitor unit 26 is electrically connected to the connecting conductor 21 which serves as connector means for the interrupting unit 23. As indicated with the preceding embodiments this capacitor unit 26 may be arranged in many other ways. Since the disconnecting switch is opened after the interrupting unit 23 has been opened, the same effect as above described will be achieved by connecting one end of the capacitor unit 26 to the movable member 84.

However, the embodiment illustrated, wherein the capacitor unit 26 is housed in the grounded tank that contains the interrupting means, has one advantage. When the disconnecting switch is in the open position, the capacitor unit 26 can be mounted and demounted while the center conductor 20 and the related parts are in operation. Conversely if the capacitor unit 26 is in the second grounded tank 3', it will be necessary to remove the gas from the tank 3' whenever the capacitor unit 26 is mounted or demounted. The degassing will reduce the interpolar dielectric strength of the disconnecting switch, and insulation will no longer be maintained. Therefore, the mounting and demounting of the capacitor unit 26 must be accomplished while the current supply to the center conductor 20 and the related parts is being cut off, too.

In all of the embodiments shown in FIGS. 1 through 10, the capacitor unit 26 is connected at one end to the connecting conductor 21, but the same effect is attained by connecting it instead to the connector means of the center conductor 20 or the like that is electrically connected to the conductor 21. In order to prepare for a short line fault on the line side, one end of the capacitor unit 26 may be connected to connector means on the line side. In other words, if the stationary contact 24 of the interrupting unit 23 is connected on the line side, the center conductor 20, stationary contact 24, and the conductor in between will combinedly form the connector means. The same applies when it is intended to prepare for a short line fault on the source side. In this connection, the closer the capacitor unit 26 is located to the interrupting unit 23, the greater the effect will be.

As described above, the capacitor unit 26 for restricting the initial rate of rise of the recovery voltage in case of a short line fault is detachably supported by the inner wall surface of the cap 6, which in turn is removably secured to the flange of an opening of the grounded tank 3 which, together with the tank 3', contains the interrupting means and the associated parts. Consequently, there is no need of using a largesize metallic tank. Moreover, the capacitor unit 26 can be mounted and demounted with extreme ease, without disassembling the interrupting means.

Especially with the embodiment illustrated in FIGS. 2 and 3, it is possible to mount the capacitor unit 26 in the circuit breaker whose flange 3*a* is closed with the cap 6, without disassembling the interrupting means, only if the interior of the insulation cylinder 22 is isolated gaswise from the interrupting means (for example, by providing seals between the connecting conductor 21 and the insulation support cylinder 22, between the insulation cylinder 22 and the disk 32, and between the connecting conductor 21 and the stationary contact 24). Stated differently, a large-capacity circuit breaker is simply obtained without modifying the construction of most of the components including the interrupting means. For the gas filling, a conduit 100 with a valve 101 is desirably arranged as indicated by dotted lines in FIG. 2 so as to establish communication, when necessary, between the hollow 22*a* of the insulation support cylinder 22 and the interior of the grounded tank 3.

Figure 11:
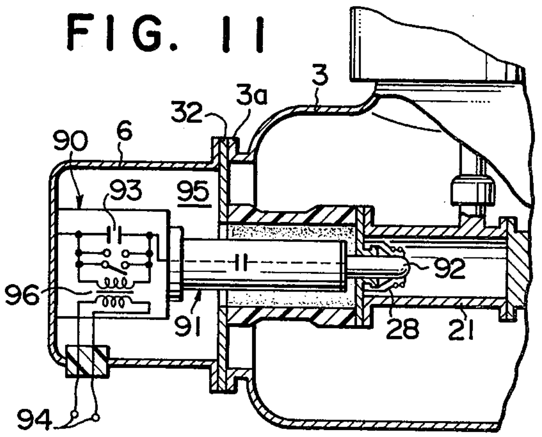

A further embodiment of the invention, as applied to a potential device, will now be explained by reference to FIG. 11.

The right hand portion of the circuit breaker not shown is, for example, the same as that of the embodiment depicted in FIG. 2.

An outwardly bulging end cap 6 is detachably secured, with an intervening disk 32, to a flange 3*a* of an opening of the grounded tank 3. To the inner surface of the cap 6 is electrically and mechanically connected a capacitor unit 95, and an electrode 92 attached to the right end of the capacitor unit 95 is electrically connected to a connecting conductor 21 through a current collector 28. The capacitor unit 95 consists of a secondary detector 90 and a primary capacitor 91. The secondary detector 90 comprises a secondary capacitor 93 and a potential transformer 96 both connected between one end of the primary capacitor 91 and the cap 6. Secondary terminals 94 of the potential transformer 96 are led out in electrical insulation from the cap 6. The secondary detector 90 is contained, for example, in an insulation case.

Like the capacitor unit 26 for controlling the initial rate of rise of the recovery voltage, the capacitor unit 95 may be arranged in the same manner as with the embodiments shown in FIGS. 1 to 10. This construction renders it possible to inspect the potential device as advantageously as with all of the preceding embodiments, for example, without the necessity of disassembling the interrupting means.

What is claimed is:

1. A grounded tank type gas circuit breaker comprising a grounded tank filled with a dielectric gas, interrupting means electrically insulated from, and mounted within, said grounded tank and including a fixed contact and a movable contact engageable and disengageable with each other, a connecting conductor arranged along the line of movement of said movable contact and mounting said fixed contact thereon, insulation support means arranged along the line of movement of said movable contact and supporting said connecting conductor in electrical insulation from said tank, said insulation support means being constructed to receive impact at the closing of said fixed and movable contacts, a sliding contact secured to said connecting conductor, an opening formed in the portion of said tank opposite to said sliding contact, means for detachably closing and sealing said opening, and a capacitor unit having an outside diameter smaller than the diameter of said opening and electrically and mechanically connected at one end to the inner wall surface of said closing and sealing means and in engagement at the other end with said sliding contact.

2. A grounded tank type gas circuit breaker according to claim 1, wherein said insulation support means is formed in a substantially hollow cylindrical shape, said sliding contact is secured to said connecting conductor at the side thereof where said conductor is connected to said insulation support means and in alignment with the axis of the hollow of said support means, said capacitor unit is arranged in the hollow of said support means, and said opening which includes therein means for connecting said insulation support means to the tank is sealed by said closing and sealing means.

3. A grounded tank type gas circuit breaker according to claim 1, wherein said insulation support means serves for protecting said capacitor unit from the impact at the closing of said fixed and movable contacts.

4. A grounded tank type gas circuit breaker according to claim 3, wherein said sliding contact also serves for protecting said capacitor unit from the impact at the closing of said fixed and movable contacts.

5. A grounded tank type gas circuit breaker according to claim 1, wherein said sliding contact serves for protecting said capacitor unit from the impact at the closing of said fixed and movable contacts.

* * * * *